(12) United States Patent
Brintle

(10) Patent No.: US 6,749,558 B1
(45) Date of Patent: Jun. 15, 2004

(54) MARITAL AID

(76) Inventor: Thomas A. Brintle, 125 Plaza Ln., Mt. Airy, NC (US) 27030

(*) Notice: Subject to any disclaimer, the term of this patent is extended or adjusted under 35 U.S.C. 154(b) by 0 days.

(21) Appl. No.: 10/371,025

(22) Filed: Feb. 20, 2003

(51) Int. Cl.[7] .................................................. A61F 5/00
(52) U.S. Cl. .......................................... 600/38; 600/41
(58) Field of Search ..................... 600/38–41

(56) References Cited

U.S. PATENT DOCUMENTS

| | | | |
|---|---|---|---|
| 4,281,648 A | 8/1981 | Rogers | |
| 4,523,584 A | 6/1985 | Yachia et al. | |
| 4,671,262 A | 6/1987 | West | |
| 4,989,592 A | 2/1991 | Chang | |
| 5,127,396 A | * 7/1992 | McAllister | 600/38 |
| 5,377,692 A | 1/1995 | Pfeil | |
| 5,445,594 A | 8/1995 | Elist | |
| 6,203,491 B1 | 3/2001 | Uribe | |

OTHER PUBLICATIONS

Adam and Eve catalog Mar. 1997, pp. 8 and 9.*
The Xandria Collection catalog, Oct. 2000, pp. 40 and 41.*

* cited by examiner

*Primary Examiner*—Samuel G. Gilbert
(74) *Attorney, Agent, or Firm*—MacCord Mason PLLC

(57) ABSTRACT

A marital aid kit comprising a plurality of semi-rigid penile extensions of varying sizes, a retainer harness attached to the penile extension to keep said penile extension in place on the male body and a sizing chart to assist the user in selecting the appropriate size penile extension for proper fit. The penile extension is constructed from a molded silicone resin and is hollow. The retainer harness contains adjustable straps to ensure proper and snug fit on the user's body. The sizing chart utilizes penis length and girth to determine appropriate size.

24 Claims, 4 Drawing Sheets

X-Vantage

Measure Length erect along the top of the penis from tip to abdomen
Measure Girth erect at the widest point, regardless of wheather it is the head or shaft
Find your size by going left to right for length and top to bottom for girth
When you connect the two lines this would be your order size

| Length> | 4.0 - 4.75 | 4.76 - 5.5 | 5.51 - 6.25 | 6.26 - 7.0 |
|---|---|---|---|---|
| Girth v | | | | |
| 3.5 - 4.0 | Green - 7 | Green - 8 | Green - 9 | Green - 10 |
| 4.10 - 4.5 | Blue - 8 | Blue - 9 | Blue - 10 | Blue - 11 |
| 4.51 - 5.0 | Orange - 9 | Orange - 10 | Orange -11 | Orange - 12 |
| 5.01 - 5.5 | Red - 10 | Red - 11 | Red - 12 | Red - 13 |
| 5.51 - 6.0 | Violet - 11 | Violet - 12 | Violet - 13 | Violet - 14 |

36 Sizing Chart
38 Length
40 Girth

FIG. 4

MARITAL AID

BACKGROUND OF THE INVENTION

The invention relates to a marital aid kit containing a penile extension with a retainer harness which can be provided in varying sizes according to the size of the erect penis of the user. Marital devices containing semi-rigid penile extensions are well known in the prior art. Phallic devices, such as dildos, have been used by women for years to produce sexual satisfaction. There have also been marital aid devices to improve sexual performance for males with difficulty in maintaining erections. These devices have been utilized to assist females in the enjoyment of the sexual act. Impotent men have resorted to aphrodisiac drugs, food supplements, and hypodermic injections to improve their sexual performance. The prior art also indicates that there have been penile extensions utilized with retaining harnesses of some type to keep these penile extensions in place over the male penis during the sexual act. These devices have provided penile rigidity necessary for female enjoyment of the sexual act for those men with erection problems. These penile extensions have been produced in a wide variety of shapes and sizes. However, the problem with the penile extensions in the prior art is that they tend to be one size fits all. These devices have failed to take into consideration the various sizes and shapes of the male users. Consequently, proper fit of the penile extension is a significant problem.

Because the existing devices tend to be one size fits all, and proper fit for the male user may be difficult there is a need in the art for a marital aid device to provide appropriate fit for the male user.

SUMMARY OF THE INVENTION

The present invention fulfills one or more of these needs by providing a marital aid kit containing a semi-rigid penile extension with a retainer harness and a sizing chart to select the appropriate size penile extension for the proper fit of the user. This marital aid device comprises a plurality of semi-rigid penile extensions of various sizes, a retainer harness attached to the penile extension to keep the penile extension in place over the penis and a sizing chart to assist the user in selecting the appropriate fit for that individual user. The penile extension is constructed from a molded supple material, primarily a silicone resin, and has the shape of a male penis, including a penis head, a penis shaft and testicle pockets. The penile extension further includes a hollow shaft, so that it can fit over the user's penis. The penile extension also has snaps. The retainer harness includes adjustable straps which are made of an elastic material and includes snaps. The retainer harness in one embodiment is affixed directly to the penile extension by the snaps on the harness being snapped directly to the snaps on the penile extension.

In another embodiment the retainer harness comprises adjustable straps with a penile extension support unit. The adjustable straps are made from an elastic material and include snaps. The penile extension support unit is made from a semi-rigid material and includes a hole in the approximate center to accommodate the penile extension. The penile extension support unit further includes snaps. The adjustable straps are snapped to the penile extension support unit and then the penile extension is placed over the penis. The straps which are around the male body are then tightened to provide a secure fit.

The marital aid kit also comprises a sizing chart which includes a penis length measurement element and a penis girth measurement element. The penis length element is determined by measuring the penis in inches along the top of an erected penis from the abdomen to the tip of the penis. The penis girth is determined by measuring the girth of an erect penis at the penis' widest point. The sizing chart includes coded penile extension sizes which are selected by utilizing the relationship between the penis length measurement and the penis girth measurement.

These and other aspects of the present invention will become apparent to those skilled in the art after reading the following description of the preferred embodiments when considered with the drawings.

BRIEF DESCRIPTION OF THE DRAWINGS

FIG. 4 is a sizing chart for obtaining proper fit of the preferred embodiment of the invention.

DETAILED DESCRIPTION OF THE PREFERRED EMBODIMENTS

Figure 1:
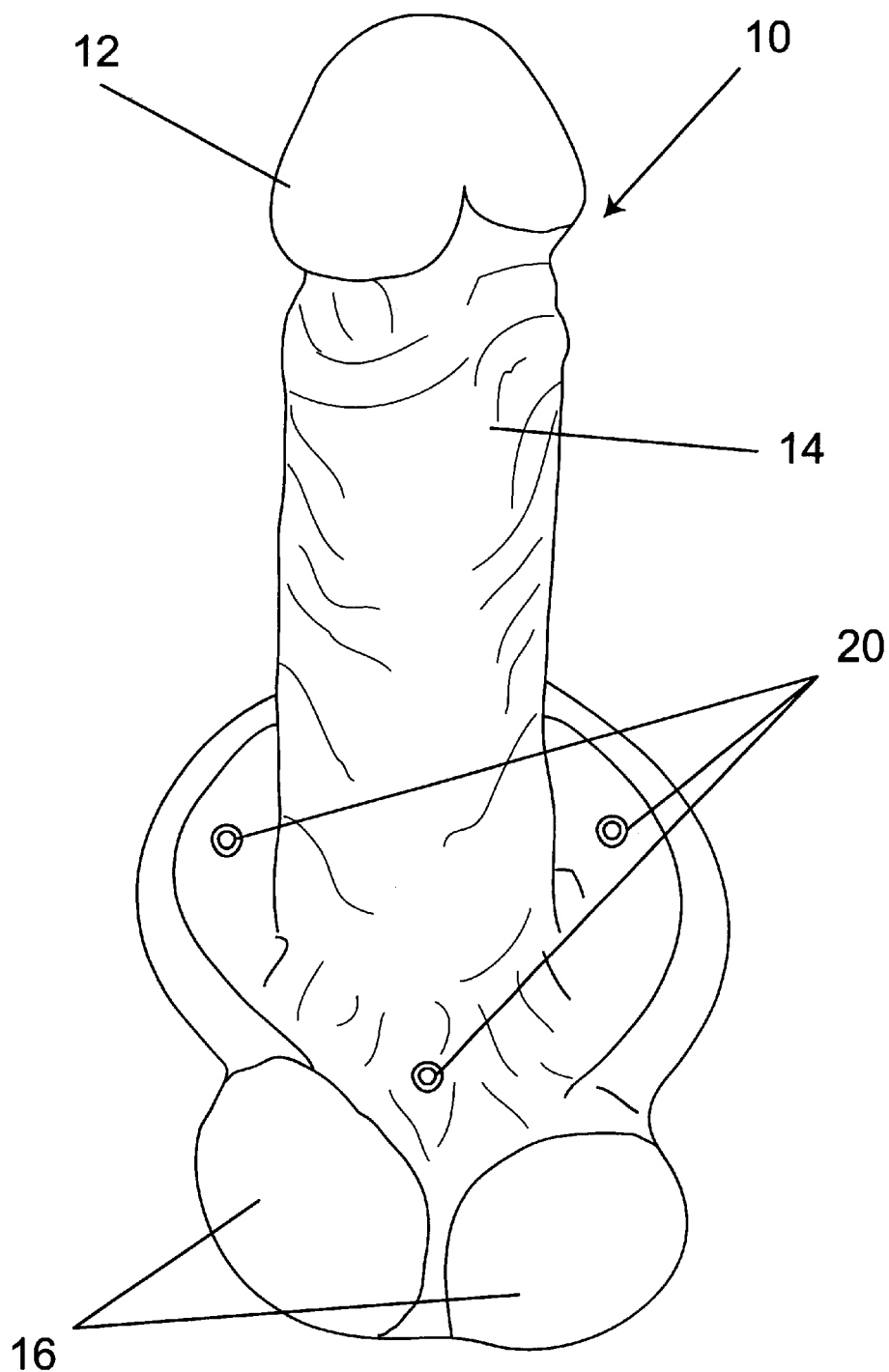
FIG. 1 is a perspective view of a component of the preferred embodiment of the invention.

In the following description, like reference characters designate like or corresponding parts throughout the several figures. It should be understood that the illustrations are for the purpose of describing preferred embodiments of the invention and are not intended to limit the invention thereto.

Figure 2:
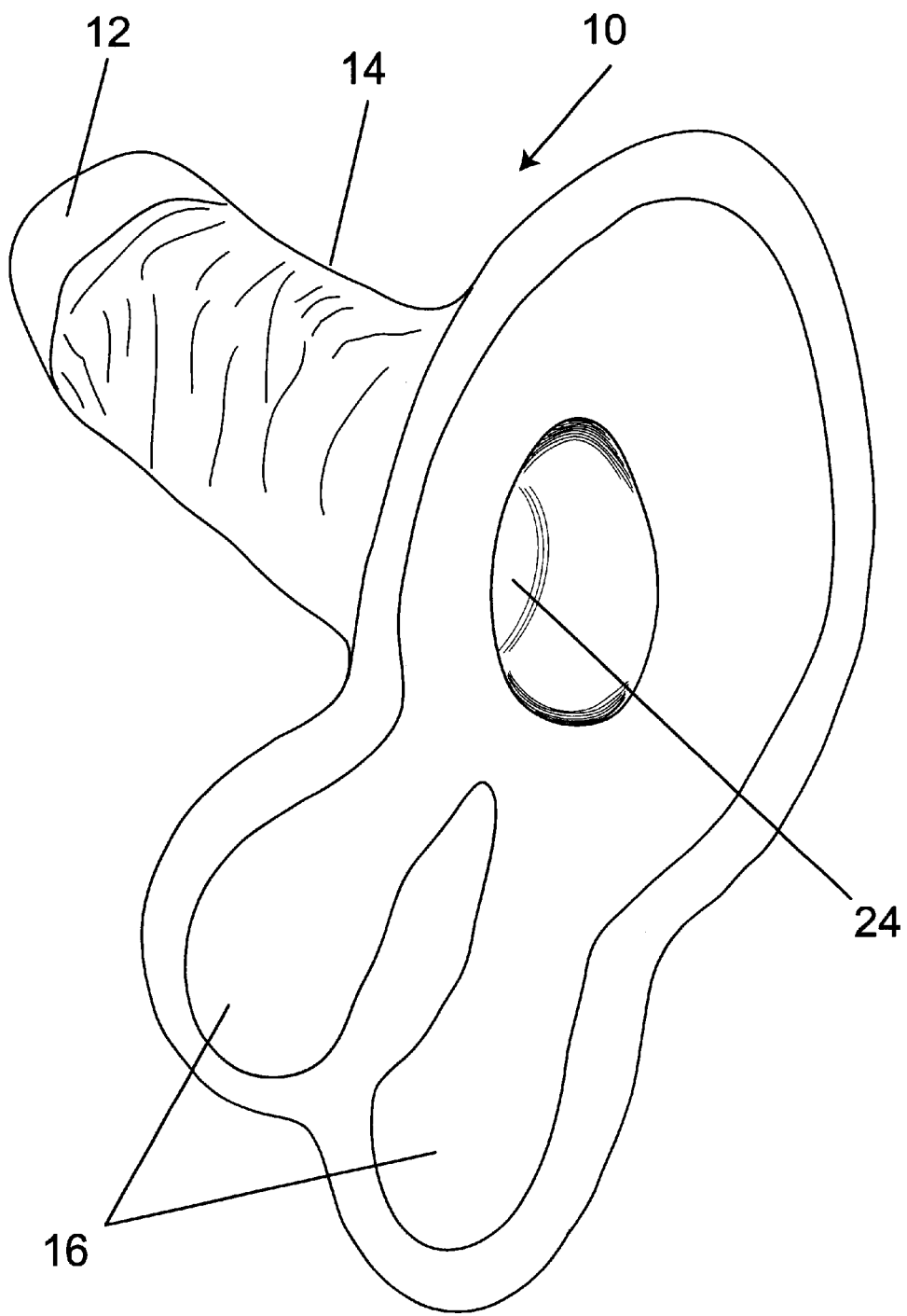
FIG. 2 is a perspective view of the penile extension depicting the hollow cavity for placement of the penis.

As best seen in FIG. 1, the penile extension 10 is represented. The penile extension 10 is semi-rigid and constructed from a molded, supple material such as a silicone resin. The penile extension 10 contains a penis head 12, a penis shaft 14 and testicle pockets 16. The testicle pockets 16 may be a shaped shell. In another embodiment the testicle pockets 16 may be molded to form a sack. The sacks may be filled with circular balls to replicate the feel of testicles during the sex act. The molded silicone resin penis extension 10 includes a hollow shaft 24, which is best seen in FIG. 2. The hollow shaft 24 provides a cavity, so that an erect penis can fit inside when the penile extension 10 is in place. The size of this cavity desirably allows the erect penis to be inserted without constriction and without causing undue movement between the silicone resin and the penis which might lead to chafing.

Figure 3:
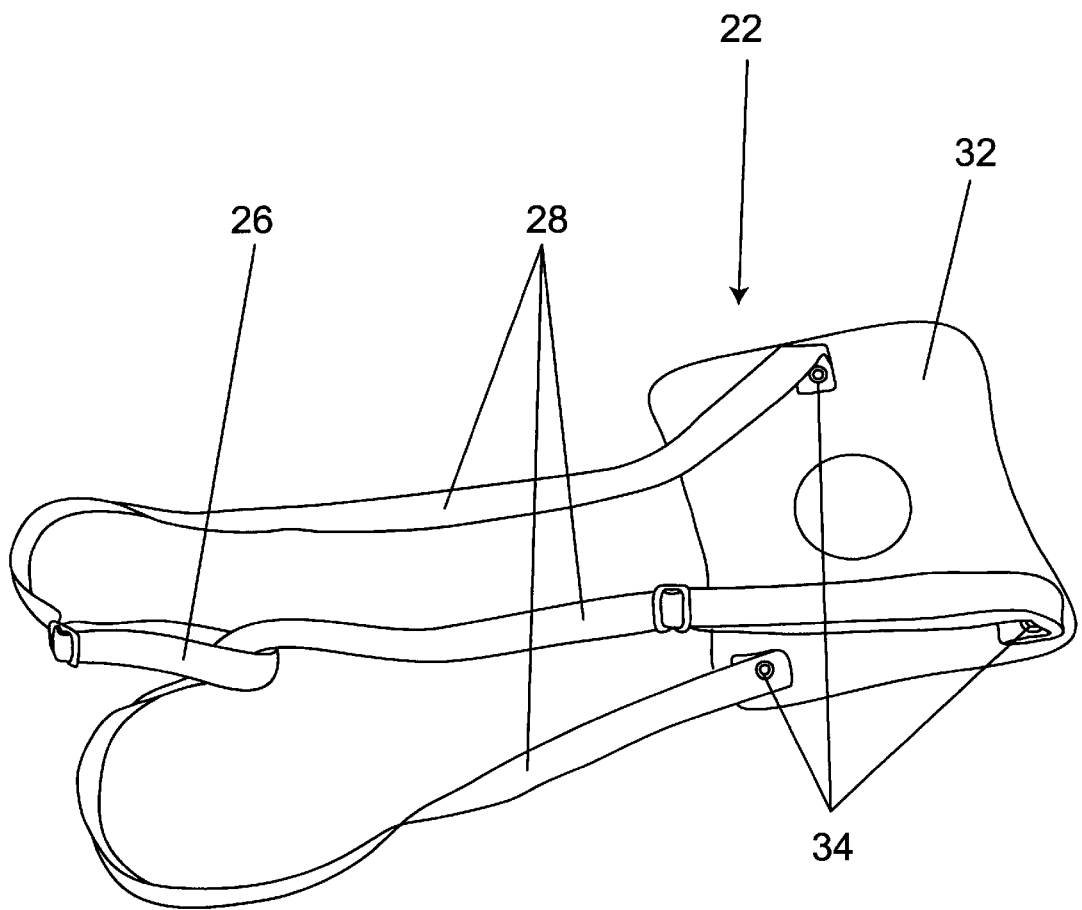
FIG. 3 is a perspective view of the attachment harness.

The penile extension 10 may further include snaps 20. These snaps 20 are utilized to affix the retainer harness 22 to the penile extension 10. The retainer harness 22 is depicted in FIG. 3 attached to an optional support member 32. The retainer harness 22 has adjustable straps 28 which are constructed of an elastic material. The adjustable straps 28 further include harness snaps 34. When the support member 32 is not used, the harness snaps 34 are affixed to the snaps 20 on the penile extension 10. In this manner, the penile extension 10 can be placed over the penis, and the adjustable straps 28 can be placed on the user's body to hold the penile extension 10 in place during the sex act. The adjustable straps 28 can be tightened to ensure a snug fit.

In an alternate embodiment, the retainer harness 22 may comprise adjustable straps 28 and a penile extension support unit 32. The adjustable straps 28 are made from elastic material and are adjustable. These adjustable straps 28 also include harness snaps 34. The penile extension support unit 32 is made from a semi-rigid material and includes a hole in the approximate center large enough to accommodate the penile extension 10. The adjustable straps 28 are snapped to the penile extension support unit 32 with the harness snaps 34. The penile extension 10 is put in place on the penis and the retainer harness 22 is placed over the penile extension 10. The adjustable straps 28 are placed on the user's body and adjusted to ensure proper fit during the sexual act.

The sizing chart depicted in FIG. 4, comprises a matrix with variable penis length 38 measurements across the top and variable penis girth 40 measurements down the left side. The penis length 38 element is determined by measuring the penis in inches along the top of an erect penis from the abdomen to the tip of the penis. The penis girth 40 element is determined by measuring the girth of an erect penis at the widest point. The sizing chart 36 further includes coded penile extension sizes which are selected by utilizing the relationship between the penis length 38 and the penis girth 40 measurements. The sizing chart 36 provides the user of the penile extension the ability to find the appropriate size for the length and girth of his penis, so that the penile extension 10 will provide the user with a proper fit during the sex act.

Depending on the suppleness and elasticity of the resin utilized to construct the penile extension 10, several sizes shown on the sizing chart 36 may interchangeably provide the proper fit. For example, referring to FIG. 4 and the sizing chart 36, Blue 8 and Green 8 may both fit the user. If so, a single size may be provided to users selecting either size, with the resilience of the extension 10 causing it to conform as needed. Again, referring to FIG. 4 and the sizing chart 36, two or more of the sizes Red 10, Orange 10, Blue 10 and Green 10 may provide a proper fit for a single user. Consequently, the more suppleness and elasticity provided in the construction of the penile extension 10, the more appropriate fit choices are available for the user. Increased suppleness and elasticity of the penile extension 10 may also eliminate the need for the 20 separate sizes shown in the sizing chart. That is, fewer sizes may provide proper fit for a wider range of users. However, this invention does not contemplate a "one size fits all" approach.

A male will measure the length and girth of his erect penis. The girth measurement will be measured at the widest point on the penis shaft and the length measurement will be measured from the abdomen along the top of the penis to the tip of the penis. These measurements will produce length and girth in inches. The sizing chart 36 contains girth and length ranges in inches. The male will determine the appropriate length and girth ranges according to his specific measurements and determine where those ranges intersect on the sizing chart 36 to determine his appropriate size.

In the preferred embodiment, the method for sale of the marital aid to the public would be the creation of a website offering the marital aid for sale. The website would be created containing product information. The sizing chart 36 should be included on the site along with instructions for its use in determining the proper size penile extension 10 to be ordered by the user. The website will contain ordering information to complete the transaction on-line. A sufficient inventory of penile extensions 10 should be kept in inventory to fill orders received on-line.

Alternate methods of sale of the marital aid would be sales in a retail store, mail order catalog, or in a television infomercial. The sizing chart 36 will be prominently displayed along with instructions for its use to assist the user in identifying the appropriate size penile extension 10 to purchase. Sales by mail order catalog and television infomercial would also contain ordering information. A sufficient inventory of marital aids of varying sizes must be maintained to provide the product for these sales.

Certain modifications and improvements will occur to those skilled in the art upon reading the foregoing description. It should be understood that all such modifications and improvements have been omitted for the sake of conciseness and readability, but are properly within the scope of the following claims.

What is claimed is:

1. A marital aid kit comprising:
   a plurality of penile extensions of varying sizes; and
   a retainer harness attached to the penile extension to keep said penile extension in place on the male body; and
   a sizing chart to assist the user in selecting the appropriate size penile extension for proper fit.

2. The apparatus according to claim 1, wherein said penile extension is constructed from a molded, supple material.

3. The apparatus according to claim 2, wherein said molded, supple material is a silicone resin.

4. The apparatus according to claim 1, wherein said penile extension is molded in the shape of a male penis comprising:
   a penis head;
   a penis shaft; and
   testicle pockets.

5. The apparatus according to claim 1, wherein said penile extension further includes a hollow shaft.

6. The apparatus according to claim 1, wherein said penile extension further includes snaps.

7. The apparatus according to claim 1, wherein said penile extension is washable.

8. The apparatus according to claim 1, further comprises a retainer harness attached to the penile extension to keep said penile extension in place on the male body.

9. The apparatus according to claim 8, wherein said retainer harness further includes adjustable straps.

10. The apparatus according to claim 9, wherein said adjustable straps are constructed of an elastic material.

11. The apparatus according to claim 9, wherein said adjustable straps further includes snaps.

12. The apparatus according to claim 11, wherein said retainer harness snaps are affixed to the snaps on said penile extension.

13. The apparatus of claim 8, wherein said retainer harness further comprises:
   adjustable straps; and
   a penile extension support unit.

14. The apparatus of claim 13, wherein said adjustable straps are made from an elastic material.

15. The apparatus of claim 13, wherein said adjustable straps further include snaps.

16. The apparatus of claim 13, wherein said penile extension support unit is made from a semi-rigid material.

17. The apparatus according to claim 13, wherein said penile extension support unit further includes a hole in the approximate center to accommodate said penile extension.

18. The apparatus according to claim 13, wherein said penile extension support unit further includes snaps.

19. The apparatus according to claim 13, wherein said adjustable straps are snapped to said penile extensions support unit.

20. The apparatus according to claim 1, wherein said sizing chart comprises a matrix having:
   a variable penis length measurement element along one axis; and
   a penis girth measurement element along another axis.

21. The apparatus according to claim 20, wherein said penis length element is determined by measuring the penis in inches along the top of an erect penis from the abdomen to the tip of the penis.

22. The apparatus according to claim 20, wherein said penis girth element is determined by measuring the girth of an erect penis at the widest point.

23. The apparatus according to claim 20, wherein said sizing chart further includes coded penile extension sizes which are selected by utilizing the relationship between the penis length measurement and the penis girth measurement.

24. A marital aid kit comprising a plurality of semi-rigid penile extensions of varying sizes, a retainer harness attached to the penile extension to keep said penile extension in place on the male body and a sizing chart to assist the user in selecting the appropriate size penile extension for proper fit.

\* \* \* \* \*